(12) United States Patent
Asada

(10) Patent No.: US 10,561,507 B1
(45) Date of Patent: Feb. 18, 2020

(54) WEARABLE GRIPPERS FOR HEMIPLEGIC PATIENTS

(71) Applicant: Boston Incubator Center, LLC, Waltham, MA (US)

(72) Inventor: Haruhiko Harry Asada, Lincoln, MA (US)

(73) Assignee: Boston Incubator Center, LLC, Lexington, MA (US)

( * ) Notice: Subject to any disclaimer, the term of this patent is extended or adjusted under 35 U.S.C. 154(b) by 0 days.

(21) Appl. No.: 15/183,677

(22) Filed: Jun. 15, 2016

Related U.S. Application Data (60) Provisional application No. 62/180,007, filed on Jun. 15, 2015, provisional application No. 62/307,563, filed on Mar. 13, 2016.

(51) Int. Cl.
*A61F 2/70* (2006.01)
*A61F 2/54* (2006.01)
(Continued)

(52) U.S. Cl.
CPC ............... *A61F 2/70* (2013.01); *A61F 2/588* (2013.01); *A61F 2/72* (2013.01); *A61F 2/78* (2013.01);
(Continued)

(58) Field of Classification Search
CPC .... A61F 2/54; A61F 2/588; A61F 2/78; A61F 2/70; B25J 9/0006
See application file for complete search history.

(56) References Cited

U.S. PATENT DOCUMENTS

| 4,623,354 A | * | 11/1986 | Childress | ................ | A61F 2/588 |
| | | | | | 623/25 |
| 4,808,187 A | * | 2/1989 | Patterson | .................. | A61F 2/72 |
| | | | | | 623/25 |

(Continued)

OTHER PUBLICATIONS

Mozaffarian D, Benjamin EJ, Go AS, et al. Heart disease and stroke statistics—2015 update: a report from the American Heart Association. Circulation. 2015; e29-322.
(Continued)

*Primary Examiner* — Bruce E Snow
(74) *Attorney, Agent, or Firm* — Spano Law Group; Joseph S. Spano (57) ABSTRACT

Methods and systems for assisting hemiplegic and hemiparetic patients are described herein. A wearable gripper system assists a user with one functional hand to independently perform basic tasks. A wearable gripper is located on the forearm above a disabled hand. The user controls the wearable gripper easily and intuitively based on gestures measured by an instrumented wristband device. Movements detected at the functioning wrist and forearm are translated into the motion control commands communicated to the actuators of the wearable gripper. In this manner, the wearable gripper assists the user to manipulate objects in lieu of the disabled hand. In some embodiments, a number of conductive, stretchable string sensors are wrapped around the hand of a user to estimate wrist and hand motion. In some embodiments, a gripper actuator includes two or more fingers, each having a location dependent shape profile and compliance to accommodate different manipulation tasks.

7 Claims, 9 Drawing Sheets

(51) Int. Cl.
| | |
|---|---|
| A61F 2/58 | (2006.01) |
| A61F 5/01 | (2006.01) |
| A61F 2/78 | (2006.01) |
| A61F 2/72 | (2006.01) |
| A61F 2/50 | (2006.01) |
| A61F 2/68 | (2006.01) |

(52) U.S. Cl.
CPC ..... *A61F 5/0118* (2013.01); *A61F 2002/5061* (2013.01); *A61F 2002/5063* (2013.01); *A61F 2002/543* (2013.01); *A61F 2002/6827* (2013.01); *A61F 2002/6872* (2013.01)

(56) References Cited

U.S. PATENT DOCUMENTS

| | | | |
|---|---|---|---|
| 9,367,139 B2* | 6/2016 | Ataee | G06F 3/017 |
| 2014/0172166 A1* | 6/2014 | Kim | B25J 3/04 |
| | | | 700/259 |
| 2015/0112450 A1* | 4/2015 | Leiniger | A61F 2/72 |
| | | | 623/36 |

OTHER PUBLICATIONS

H. Kazerooni and R. Steger, "The Berkeley lower extremity exoskeleton," ASME Trans J of Dynamic Systems, Measurements, and Control, vol. 12, pp. 14-25, 2006.
K. Kong and D. Jeon, "Design and control of an exoskeleton for the elderly and patients," IEEE Trans Neural Syst Rehabil Eng., vol. 15, No. 3, pp. 367-378, 2006.
J. A. Blay and H. Herr, "Control of a variable-M̂impedance ankle-M̂foot orthosis to assist drop-foot gait," IEEE Trans Neural Syst Rehabil Eng, vol. 12, No. 1, pp. 24-31, 2004.
K. Yamamoto, M. Ishii, K. Hyodo, and T. Yoshimitsu, T. Matsuo, "Development of power assisting suit (miniaturization of supply system to realize wearable suit)", JSME Int. J., vol. 46, No. 3, pp. 923-930, 2003.
J.E. Pratt, B. T. Krupp, C. J. Morse, and S.H. Collins, "The RoboKnee: an exoskeleton for enhancing strength and endurance during walking," in Proc. of IEEE International Conference on Robotics and Automation (ICRA), New Orleans, LA, 2004, pp. 2430-2435.
M. DiCicco, L. Lucas, and Y. Matsuoka, "Comparison of control strategies for an EMG controlled orthotic exoskeleton or the hand," in Proc. of IEEE International Conference on Robotics and Automation (ICRA), New Orleans, LA, 2004, pp. 1622-1627.
Y. Hasegawa, Y. Mikami, K. Watanabe, Z. Firouzimehr, and Y. Sankai, "Wearable handling support system for paralyzed patient," in Proc. of IEEE/RSJ International Conference on Intelligent Robots and Systems (IROS), Sep. 2008, pp. 741-746.
K. In, D. Lee and K.-M̂J. Cho, "Investigation of friction characteristics of a tendon driven wearable robotic hand," in Proc. of International Conference on Control Automation and Systems (ICCAS), Oct. 2010, pp. 568-573.
P. F. M. Sale, S. Mazzoleni, E. Palma, M. Agosti, and F. Posteraro, "Effects of upper limb robot-assisted therapy on motor recovery in subacute stroke patients," J Neuroeng Rehabil., vol. 11, No. 104, pp. 111-121, 2014.
S. Mazzoleni, M. Filippi, M. Carrozza, F. Posteraro, L. Puzzolante and E. Falchi, "Robot-aided therapy on the upper limb of subacute and chronic stroke patients: A biomechanical approach," in Proc. of IEEE International Conference on Rehabilitation Robotics (ICORR), Zurich, Switzerland, 2011.
A. Basteris, A. De Luca, V. Sanguineti, C. Solaro, M. Mueller, I. Carpinella, D. Cattaneo, R. Bertoni, and M. Ferrarin, "A tailored exercise of manipulation of virtual tools to treat upper limb impairment in Multiple Sclerosis," in Proc. of IEEE International Conference on Rehabilitation Robotics (ICORR), Zurich, Switzerland, 2011.

B. Llorens-Bonilla, F. Parietti, and H. Asada, "Demonstration-based control of supernumerary robotic limbs," in Proc. of IEEE/RSJ International Conference on Intelligent Robots and Systems (IROS), Vilamoura, Portugal, 2012, pp. 3936-3942.
B. Llorens-Bonilla and H. Asada, "Control and Coordination of Supernumerary Robotic Limbs based on Human Motion Detection and task Petri Net," in Proc. of ASME Dynamic Systems and Control Conference (DSCC), Palo Alto, CA, 2013.
F. Parietti and H. Asada, "Dynamic Analysis and State Estimation for Wearable Robotic Limbs Subject to Human-Induced Disturbances," in Proc. of IEEE International Conference on Robotics and Automation (ICRA), Karlsruhe, Germany, May 2013.
B. Llorens-Bonilla and H. Asada, "A Robot on the Shoulder: Coordinated Human-Wearable Robot Control using Coloured Petri Nets and Partial Least Squares Predictions," in Proc. IEEE International Conference on Robotics and Automation (ICRA), Hong Kong, China, May 2014.
F. Parietti and H. Asada, "Supernumerary Robotic Limbs for Aircraft Fuselage Assembly: Body Stabilization and Guidance by Bracing," in Proc. of IEEE International Conference on Robotics and Automation (ICRA), Hong Kong, China, May 2014.
F. Parietti and H. Asada, "Bracing the Human Body with Supernumerary Robotic Limbs for Physical Assistance and Load Reduction," in Proc. of IEEE International Conference on Robotics and Automation, (ICRA), Hong Kong, China, May 2014.
F.Y. Wu and H. Asada, "Bio-Artificial Synergies for Grasp Control of Supernumerary Robotic Fingers," in Robotics: Science and Systems X (RSS), Berkeley, CA, 2014.
F.Y. Wu and H. Asada, "Supernumerary Robotic Fingers: an Alternative Upper Limb Prosthesis," in Proc. of ASME Dynamic Systems and Control Conference (DSCC), San Antonio, TX, 2014.
Minino AM, Murphy SL, Xu J, Kochanek KD. Deaths: final data for 2008. Natl Vital Stat Rep 2011; 59(10).
Kelly-Hayes M, Beiser A, Kase CS, Scaramucci A, D'Agostino RB, Wolf PA. The influence of gender and age on disability following ischemic stroke: the Framingham Study. J Stroke Cerebrovasc Dis 2003; 12:119-26.
Kai-Nan An, Richard A. Berger, William P. III Cooney (editors and authors), "Biomechanics of the wrist joint", Springer-Verlag, New York, 1991.
F. Hammond III, Y. Menguc, and R. Wood. "Toward a Modular Soft Sensor-M̂Embedded Glove for Human Hand Motion Measurement", in Proc. of IEEE/RSJ International Conference on Intelligent Robots and Systems (IROS), 2014.
Sofia, K.O. & Jones, L.A., "Mechanical and psychophysical studies of surface wave propagation during vibrotactile stimulation", in IEEE Transactions on Haptics, 6, 320-329, 2013.
H. Hanafusa and H. Asada, "Stable Prehension by a Robotic Hand with Elastic Fingers," in Proc. of Int. Symp. on Industrial Robots, Tokyo, Japan, Oct. 1977, pp. 361-367.
J. K. Salisbury and J. J. Craig, "Articulated hands: force control and kinematic issues," in Proc. of Joint Automatic Control Conference, Charlottesville, VA, 1981, vol. 1, pp. TA-2C/1-9.
K. Lakshminarayana, "Mechanics of Form Closure," ASME Technical paper 78-DET-M̂32, 1978.
E. Rimon and J. Burdick, "On Force and Form Closure for Multiple Finger Grasps", in Proc. of IEEE International Conference on Robotics and Automation (ICRA), Minneapolis, MN, 1996.
Y.-C. Chen, I. D. Walker, and J. B. Cheatham, "A new approach to force distribution and planning for multifingered grasps of solid objects," in Proc. of IEEE International Conference on Robotics and Automation (ICRA), Sacramento, CA, 1991, vol. pp. 890-896.
A. Shapiro, E. Rimon, and J. W. Burdick, "On the mechanics of natural compliance in frictional contacts and its effect on grasp stiffness and stability," in Proc. of IEEE International Conference on Robotics and Automation (ICRA), 2004, New Orleans, LA, vol. 2, pp. 1264-1269.
J. T. Belter and A. M. Dollar, "Underactuated Grasp Acquisition and Stability Using Friction Based Coupling Mechanisms," in Proc. of IEEE International Conference on Robotics and Automation (ICRA), Shanghai, China, 2011, pp. 3035-3040.
Gibbs, T., and Asada, H., "Wearable Conductive Fiber Sensors for Multi-M̂Axis Human Joint Angle Measurements", Journal of (56) References Cited

OTHER PUBLICATIONS

Neuroengineering and Rehabilitation, 2:7, Mar. 2, 2005. Special Issue on Wearable Technology in Rehabilitation, Feb. 2005.

S. L. Delp, G. M. Nielsen, and R. C. Wood, "Design, development, and evaluation of a new body-powered arm prosthesis," in Proc. of Conference on Rehabilitation Engineering (RESNA), Minneapolis, MN, 1986, pp. 123-125.

R. F. Weir and E. C. Grahn, "Development of externally-powered prostheses for persons with partial hand amputations," in Proc. of International Conference of the IEEE Engineering in Medicine and Biology (EMBS), Chicago, IL, 2000, pp. 427-430.

J. Zariffa, N. Kapadia, J. L. K. Kramer, P. Taylor, M. Alizadeh-M Meghrazi, V. Zivanovic, R. Willms, A. Townson, A. Curt, M. Popovic, and J. Steeves, "Effect of a robotic rehabilitation device on upper limb function in a sub-Macute cervical spinal cord injury population," in Proc. of IEEE International Conference on Rehabilitation Robotics (ICORR), Zurich, Switzerland, 2011.

C. Davenport, F. Parietti, and H. Asada, "Design and Biomechanical Analysis of Supernumerary Robotic Limbs," in Proc. of ASME Dynamic Systems and Control Conference (DSCC), Fort Lauderdale, FL, 2012.

Roger VL, Go AS, Lloyd-Jones DM, et al. Heart disease and stroke statistics—2012 update: a report from the American Heart Association. Circulation 2012; 125:e2-220.

\* cited by examiner

WEARABLE GRIPPERS FOR HEMIPLEGIC PATIENTS

CROSS REFERENCE TO RELATED APPLICATIONS

The present application for patent claims priority under 35 U.S.C. § 119 from U.S. provisional patent application Ser. No. 62/180,007, entitled "Wearable Grippers For Hemiplegic Patients," filed Jun. 15, 2015, and from U.S. provisional patent application Ser. No. 62/307,563, entitled "Measuring Hand Gesture Using Conductive String Sensors," filed Mar. 13, 2016, the subject matter of each is incorporated herein by reference in its entirety.

TECHNICAL FIELD

The described embodiments relate to systems and methods for hand gesture measurement and wearable manipulators to assist disabled patients.

BACKGROUND INFORMATION

Hemiplegia and hemiparesis may be caused by various illnesses, including Parkinson's disease, multiple sclerosis, spinal cord injury, traumatic brain injury, cerebral palsy, poliomyelitis, and arthritis. In addition, over eight hundred thousand Americans suffer a stroke every year, leaving many hemiplegic or hemiparetic. Damage suffered in one side of the brain often causes disability to limbs on the opposite side. An increasing population of stroke survivors, and others, are facing enormous difficulties in performing daily chores, and many require assistance from others. The cost of care for stroke survivors, including lost productivity and premature mortality, is enormous.

In many cases, rehabilitation training remains the sole therapeutic approach to recover lost motor skills. The majority of stroke patients who initiate rehabilitation therapy soon after a stroke are able to regain a significant amount of motor function. In some examples, a recovery of motor function at the shoulder is achieved in two to three weeks, and a recovery of motor function at the elbow is achieved in six to eight weeks. However, recovery of motor function at the wrist and fingers is more difficult. For patients who start their training in a later stage of disability, the recovery of lost function is often limited, resulting in chronic hemiplegia or hemiparesis. As the benefits of treatment begin to fade, rehabilitation therapy is ultimately terminated. Patients who are left hemiplegic or hemiparetic are often placed at skilled nursing facilities, rather than returning home.

Wearable robots have been studied for rehabilitation and assistance of those suffering from disability. In some examples, prosthetic devices substitute lost biological limbs with mechanical proxies. Prosthetic devices improve the quality of life of amputees, but they are not applicable to hemiplegic and hemiparetic patients whose impaired arms and hands are still physically attached to their body. In other examples, exoskeleton devices extend strength and endurance by attaching actuators to individual human joints. Orthotic exoskeletons may help restore lost limb functions, but most are developed for patients with lower extremity disabilities. The few devices designed to aid the weakened hand are highly complex, bulky, uncomfortable, and limited in performance. These include a pneumatically actuated device that is controlled by electromyography (EMG) to achieve pinching actions described by M. DiCicco, et al., "Comparison of control strategies for an EMG controlled orthotic exoskeleton for the hand," in Proc. of IEEE International Conference on Robotics and Automation (ICRA), New Orleans, La., 2004, pp. 1622-1627; tendon-driven rigid frames that monitor head motion to perform pouring tasks described by Y. Hasegawa, et al., "Wearable handling support system for paralyzed patient," in Proc. of IEEE/RSJ International Conference on Intelligent Robots and Systems (IROS), September 2008, pp. 741-746; and a frameless device with a modified differential mechanism activated by wrist movement to tighten a grip described by K. In, et al., "Investigation of friction characteristics of a tendon driven wearable robotic hand," in Proc. of International Conference on Control Automation and Systems (ICCAS), October 2010, pp. 568-573.

More often, upper limb exoskeleton devices are employed for robot-assisted rehabilitation treatment. These therapies have been shown to increase motor recovery in patients suffering from 1) subacute and chronic stroke as described by P. F. M. Sale, et al., "Effects of upper limb robot-assisted therapy on motor recovery in subacute stroke patients," J Neuroeng Rehabil., vol. 11, no. 104, pp. 111-121, 2014 and S. Mazzoleni, et al., "Robot-aided therapy on the upper limb of subacute and chronic stroke patients: A biomechanical approach," in Proc. of IEEE International Conference on Rehabilitation Robotics (ICORR), Zurich, Switzerland, 2011, 2) subacute cervical spinal cord injury described by J. Zariffa, et al., "Effect of a robotic rehabilitation device on upper limb function in a sub-acute cervical spinal cord injury population," in Proc. of IEEE International Conference on Rehabilitation Robotics (ICORR), Zurich, Switzerland, 2011, and 3) multiple sclerosis described by A. Basteris, et al., "A tailored exercise of manipulation of virtual tools to treat upper limb impairment in Multiple Sclerosis," in Proc. of IEEE International Conference on Rehabilitation Robotics (ICORR), Zurich, Switzerland, 2011.

While exoskeleton devices show great promise for rehabilitation training, they are not applicable to assisting hemiplegic patients at home. For example, the application of an external force or torque to an affected finger may be dangerous unless it is executed under supervision of a professional. In many cases, the disabled fingers have severely limited tactile function or are completely numb. With limited sensitivity, a patient may be unaware that an externally applied force or torque is damaging their disabled finger.

Despite advances in the design and control of wearable robots, neither prosthetic devices nor exoskeleton devices meet the requirements for assisting chronic hemiplegic or hemiparetic patients at home.

In another example, supernumerary robotic (SR) limbs are attached to the body to assist a patient to hold objects, support body weight, and streamline task execution described by B. Llorens-Bonilla, et al., "Demonstration-based control of supernumerary robotic limbs," in Proc. of IEEE/RSJ International Conference on Intelligent Robots and Systems (IROS), Vilamoura, Portugal, 2012, pp. 3936-3942; C. Davenport, et al., "Design and Biomechanical Analysis of Supernumerary Robotic Limbs," in Proc. of ASME Dynamic Systems and Control Conference (DSCC), Fort Lauderdale, Fla., 2012; B. Llorens—Bonilla and H. Asada, "Control and Coordination of Supernumerary Robotic Limbs based on Human Motion Detection and task Petri Net," in Proc. of ASME Dynamic Systems and Control Conference (DSCC), Palo Alto, Calif., 2013; F. Parietti and H. Asada, "Dynamic Analysis and State Estimation for Wearable Robotic Limbs Subject to Human-Induced Disturbances," in Proc. of IEEE International Conference on Robotics and Automation (ICRA), Karlsruhe, Germany, May 2013; B. Llorens—Bonilla and H. Asada, "A Robot on the Shoulder: Coordinated Human-Wearable Robot Control using Coloured Petri Nets and Partial Least Squares Predictions," in Proc. IEEE International Conference on Robotics and Automation (ICRA), Hong Kong, China, May 2014; F. Parietti and H. Asada, "Supernumerary Robotic Limbs for Aircraft Fuselage Assembly: Body Stabilization and Guidance by Bracing," in Proc. of IEEE International Conference on Robotics and Automation (ICRA), Hong Kong, China, May 2014; F. Parietti and H. Asada, "Bracing the Human Body with Supernumerary Robotic Limbs for Physical Assistance and Load Reduction," in Proc. of IEEE International Conference on Robotics and Automation, (ICRA), Hong Kong, China, May 2014; F. Y. Wu and H. Asada, "Bio-Artificial Synergies for Grasp Control of Supernumerary Robotic Fingers," in Robotics: Science and Systems X (RSS), Berkeley, Calif., 2014; and F. Y. Wu and H. Asada, "Supernumerary Robotic Fingers: an Alternative Upper Limb Prosthesis," in Proc. of ASME Dynamic Systems and Control Conference (DSCC), San Antonio, Tex., 2014.

In one example, a set of wrist-mounted supernumerary robotic (SR) fingers attached to a functional hand augments the functionality of the same functional hand to perform tasks that typically require two hands. This may be applicable to hemiparetic or hemiplegic patients left with a single functional hand.

SR fingers have some advantages. For example, no torque is applied to a disabled human finger, and the SR fingers can safely generate a large force. Unlike exoskeleton devices, SR Fingers are not constrained to affected, disabled fingers. SR fingers can assume an arbitrary posture that is independent of the affected fingers. This allows an SR finger to assist in the performance of daily tasks that are difficult to perform with a finger exoskeleton. A SR finger can touch a hot object that would otherwise burn affected, insensitive fingers. In contrast, a finger exoskeleton device would force the insensitive, affected fingers to grasp the hot object directly.

Unfortunately, the SR fingers described with reference to the articles mentioned hereinbefore are mechanically complex. In addition, the human-robot communication techniques are highly sophisticated and require complex user training. An instrumented glove is utilized to measure the hand gestures that form the basis for control of the SR fingers. A number of hand gesture measurement products have been developed, including a finger mount glove for computer input applications (e.g., the Gest wearable device) and numerous sensory gloves for operating robots or machines. Most of these gloves are built with sophisticated sensors and complex integrated circuits that measure movement, orientation, and configuration of the hand. For applications that only require a simple interpretation of hand gesture, e.g., opening or closing of the hand, these gloves are too costly. In addition, the user of the wearable glove cannot use their hands to perform regular tasks, e.g., picking up small items and washing hands, while wearing the glove. For at least these reasons, the wearable gloves and SR fingers described with reference to the aforementioned articles are unsuitable for general home use applications.

In summary, improvements in wearable hand gesture sensors and in the design and control of wearable robotic devices are desired to provide rehabilitation and assistance to people suffering from chronic hemiplegic or hemiparetic disabilities.

SUMMARY

Methods and systems for assisting hemiplegic and hemiparetic patients are described herein. A wearable gripper system assists a user with one functional hand to independently perform basic tasks. A large number of tasks may be accomplished with one hand holding an object while another hand manipulates some element of the object.

In one aspect, a wearable gripper is located on the forearm above a disabled hand. The user controls the wearable gripper easily and intuitively based on gestures measured by an instrumented wristband. Natural and intuitive movements at the functioning wrist and forearm are translated into the motion control commands. The motion control commands are communicated to the actuators of the wearable gripper. In this manner, the wearable gripper assists the user to manipulate objects in lieu of the disabled hand. In some examples, the wearable gripper works together with the opposite, functional hand to perform various tasks (e.g., use a walker stably, hold a bottle and open the lid, independently perform dressing and undressing tasks, etc.).

In another aspect, an instrumented wristband device includes gesture sensors such as an inertial measurement unit (IMU) and a wrist goniometer 223. The instrumented wristband device does not cover the fingertips, nor does it interfere with movements of the fingers and palm. The instrumented wristband device is configured to detect movements of a user. The signals generated by the instrumented wristband device are received by a wearable gripper control and power management module (WGCPMM). WGCPMM generates control commands for controlling a wearable gripper device based on the measured gesture signals. Control algorithms translate wristband sensor signals to gripper motion commands such that the correlation between gesture and gripper motion is intuitive. In this manner, the interface between a user and a wearable gripper system is natural and easy to use. In a further aspect, the control algorithms which translate wristband sensor signals to gripper motion commands are different depending on the disability level of each user.

In a further aspect, a number of conductive, stretchable string sensors wrapped around the hand or fingers of a user are employed to estimate wrist and hand motion.

In another further aspect, a gripper actuator includes two or more fingers, each having a location dependent shape profile and compliance to accommodate different manipulation tasks.

In another further aspect, a force sensor is located on the wearable gripper to measure the amount of force applied by the gripper onto an object. In some embodiments, the measured force is read from the force sensor by a WGCPMM. The WGCPMM generates command signals that cause the measured force to be rendered by a device such as a display device or a haptic rendering device.

In another further aspect, one or more temperature sensors are located on the wearable gripper to measure the temperature of objects in contact with the wearable gripper. In some embodiments, the measured temperature is read from the temperature sensor by a WGCPMM. The WGCPMM generates command signals that cause the measured temperature to be rendered by a device such as a display device or a haptic rendering device.

In another further aspect, an image capture device is located on the gripper. In one example, the image capture device collects images of medicine labels and transmits the images electronically to health care providers for verification or refill. In another example, the image capture device collects images and the images are rendered on a large format, external display device. In this manner, users with impaired vision are able to view large format images of their surroundings.

The foregoing is a summary and thus contains, by necessity, simplifications, generalizations, and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for assisting hemiplegic and hemiparetic patients are described herein. A wearable gripper system assists a user with one functional hand to independently perform basic tasks. A large number of tasks may be accomplished with one hand holding an object while another hand manipulates some element of the object. Exemplary tasks include opening a bottle, can, container, etc., cutting food items with a knife, washing dishes, dispensing tooth paste on a tooth brush, opening and closing a door while holding another item, etc. These tasks may be performed with one hand holding an object while the other hand, i.e., a fully functional hand, performs more complex manipulative tasks.

In one aspect, a wearable gripper is located on the forearm above a disabled hand. The user controls the wearable gripper easily and intuitively based on gestures measured by an instrumented wristband. Natural and intuitive movements at the functioning wrist and forearm are translated into the motion control commands. The motion control commands are communicated to the actuators of the wearable gripper. In this manner, the wearable gripper assists the user to manipulate objects in lieu of the disabled hand. In some examples, the wearable gripper works together with the opposite, functional hand to perform various tasks (e.g., use a walker stably, hold a bottle and open the lid, independently perform dressing and undressing tasks, etc.).

Figure 1:
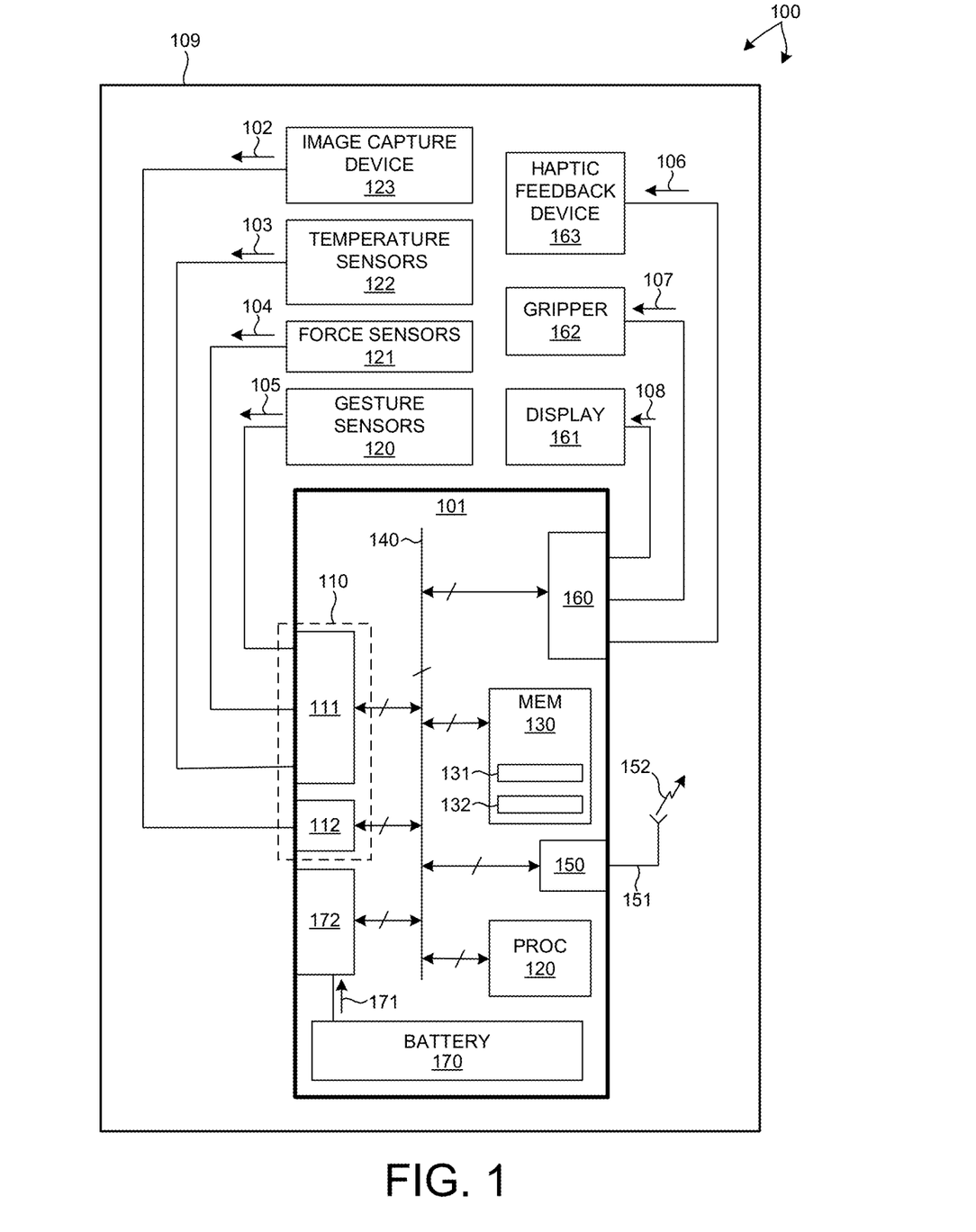
FIG. 1 is a diagram illustrative of an embodiment of a wearable gripper system 100 in at least one novel aspect.

FIG. 1 is a diagram illustrative of an embodiment of a wearable gripper system 100 including a removable brace 109, one or more gesture sensors 120, a wearable gripper control and power management module (WGCPMM) 101, and a gripper device 162. The gripper device 162 is mechanically coupled to the brace 109. In other embodiments, any of the other elements depicted in FIG. 1 are also mechanically coupled to brace 109.

In the embodiment depicted in FIG. 1, WGCPMM 101 is communicatively coupled to gesture sensors 120 and gripper 162 by a wired communications link. However, in general, WGCPMM 101 may be communicatively coupled to any of the sensors and devices described herein by either a wired or wireless communication link.

Removable brace 109 is configured to be removeably coupled to the forearm of a user of wearable gripper system 100. When removable brace 109 is coupled to the forearm of the user, gripper device 162 is positioned with respect to the wrist and hand of the human user. In some embodiments, one or more gesture sensors 120 are integrated with an instrumented wristband device that is itself integrated with brace 109. In these embodiments, gesture sensors 120 are positioned with respect to the wrist and hand of the human user when removable brace 109 is coupled to the forearm of the user. In some other embodiments, one or more gesture sensors 120 are integrated with an instrumented wristband device that is not integrated with brace 109. In these embodiments, gesture sensors 120 are positioned with respect to the wrist and hand of the human user when the instrumented wristband device is coupled to the wrist and hand of the human user.

As depicted in FIG. 1, one or more force sensors 121, one or more temperature sensors 122, an image capture device 123, a haptic feedback device 163, and a display device 161 are also communicatively coupled to WGCPMM 101. These particular sensors and devices are presented by way of example, and their inclusion as elements of a wearable gripper system is optional.

In general, any number of sensors attached to the human user to monitor position and physical status of the arm, wrist, and hand of the user may be communicatively coupled to WGCPMM 101.

As depicted in FIG. 1, WGCPMM 101 includes a sensor interface 110, a processor 120, a memory 130, a bus 140, a wireless communication transceiver 150, a power supply 172, a controlled device interface 160, and a battery 170. Sensor interface 110, processor 120, memory 130, wireless communication transceiver 150, power supply 172, and controlled device interface 160 are configured to communicate over bus 140.

Sensor interface 110 includes analog to digital conversion (ADC) electronics 111. In addition, in some embodiments, sensor interface 110 includes a digital input/output interface 112. In some other embodiments, sensor interface 110 includes a wireless communications transceiver (not shown) configured to communicate with a sensor to receive measurement data from the sensor.

As depicted in FIG. 1, ADC 111 is configured to receive analog signal 105 from each gesture sensor 120. In another non-limiting example, ADC 111 is configured to receive analog signals 104 from each force sensor 121. In yet another non-limiting example, ADC 111 is configured to receive analog signals 103 from each temperature sensor 122. ADC 111 is further configured to convert the analog signal 105 into an equivalent digital signal suitable for digital storage and further digital processing. ADC 111 is selected to ensure that the resulting digital signal is a suitably accurate representation of the incoming analog signals (i.e., quantization and temporal discretization errors are within acceptable error levels).

As depicted in FIG. 1, digital I/O 112 is configured to receive digital signals 102 from image capture device 123. In this example, image capture device 123 includes on-board electronics to generate digital signals 102 indicative of the detected images. In this manner, WGCPMM 101 is configured to interface with both analog and digital sensors. In general, any of the sensors described herein may be digital or analog sensors, and may be communicatively coupled to WGCPMM 101 by the appropriate interface.

Controlled device interface 160 includes appropriate digital to analog conversion (DAC) electronics. In addition, in some embodiments, controlled device interface 160 includes a digital input/output interface. In some other embodiments, controlled device interface 160 includes a wireless communications transceiver configured to communicate with a device, including the transmission of control signals. As depicted in FIG. 1, controlled device interface 160 is configured to transmit control commands 107 to the gripper device 162. In another non-limiting example, controlled device interface 160 is configured to transmit control commands 106 to haptic feedback device 163. In yet another non-limiting example, controlled device interface 160 is configured to transmit data signals 108 to display device 161.

Memory 130 includes an amount of memory 131 that stores measurement data collected from sensors 120-122 and image capture device 123. Memory 130 also includes an amount of memory 132 that stores program code that, when executed by processor 120, causes processor 120 to implement WGCPMM functionality as described herein.

In some examples, processor 120 is configured to store digital signals generated by sensor interface 110 onto memory 131. In addition, processor 120 is configured to read the digital signals stored on memory 131 and transmit the digital signals to wireless communication transceiver 150. Wireless communications transceiver 150 is configured to communicate the digital signals from WGCPMM 101 to an external computing device (not shown) over a wireless communications link. As depicted in FIG. 1, wireless communications transceiver transmits a radio frequency signal 152 over antenna 151. The radio frequency signal 152 includes digital information indicative of the digital signals to be communicated from WGCPMM 101 to the external computing device. In one example, images collected by image capture device 123 are communicated to an external computing system for purposes of monitoring the activities of the user.

In some embodiments, memory 131 is removably coupled to WGCPMM 101 and is further configured such that the digital signals stored on memory 131 are readable from memory 131 by another electronic device. In this manner, data stored in memory 131 can be accessed by removing memory 131 from WGCPMM 101 and downloading the data onto another computing system. In some embodiments, memory 131 is a solid-state memory device in any of a number of commonly available formats (e.g., Compact-Flash, miniSD, etc.). In other embodiments, memory 131 is a miniature hard drive (e.g., a Microdrive, etc.). In general, any removable memory format may be contemplated.

In a further aspect, WGCPMM 101 is configured to supply electrical power to one or more sensors. As depicted in FIG. 1, WGCPMM 101 includes a battery 170 that supplies power to electronic components of WGCPMM 101. However, battery 170 is also configured to supply electrical power 171 to power supply 172. Power supply 172 is configured supply electrical power signals to sensors coupled to WGCPMM 101. Power supply 172 is attached to bus 140 and is controlled by processor 120. Processor 120 is configured to detect the power supply requirements (if any) of each attached sensor and configure power supply 172 to supply appropriate electrical power signals.

Figure 2:
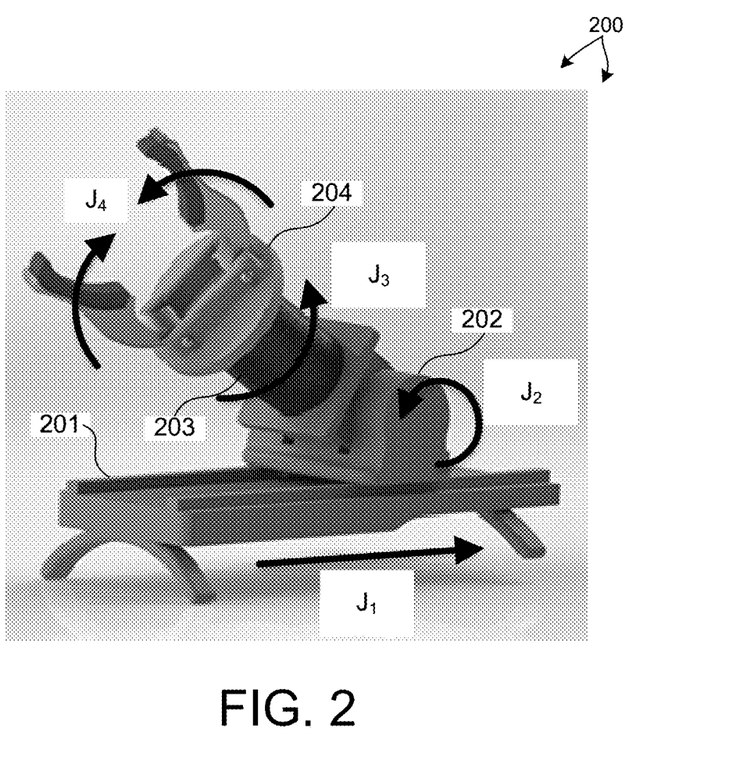
FIG. 2 depicts an embodiment 200 of a wearable gripper device.
Figure 3:
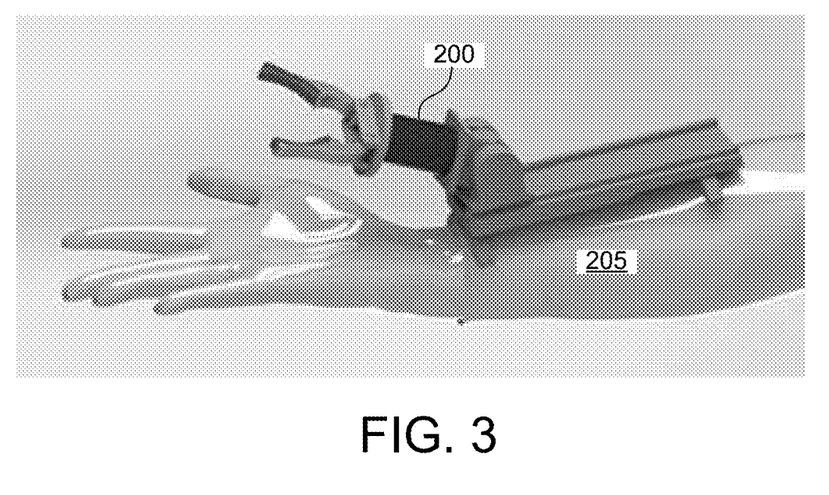
FIG. 3 depicts wearable gripper device 200 attached to the forearm 205 of a human user.

FIG. 2 depicts an embodiment 200 of a wearable gripper device by way of non-limiting example. Wearable gripper device 200 is a two-fingered gripper that can hold a variety of objects at diverse postures with a regulated force in a required force range. Wearable gripper device 200 is a four degree-of-freedom device that includes prismatic actuator 201 capable of generating linear motion characterized by joint, $J_1$, rotary actuator 202 capable of generating rotary motion characterized by joint, $J_2$, rotary actuator 203 capable of generating rotary motion characterized by joint, $J_3$, and gripper actuator 204 capable of generating the coordinated rotary motion of the gripper fingers characterized by joint, $J_4$. FIG. 3 depicts wearable gripper device 200 attached to the forearm 205 of a human user.

Figure 4:
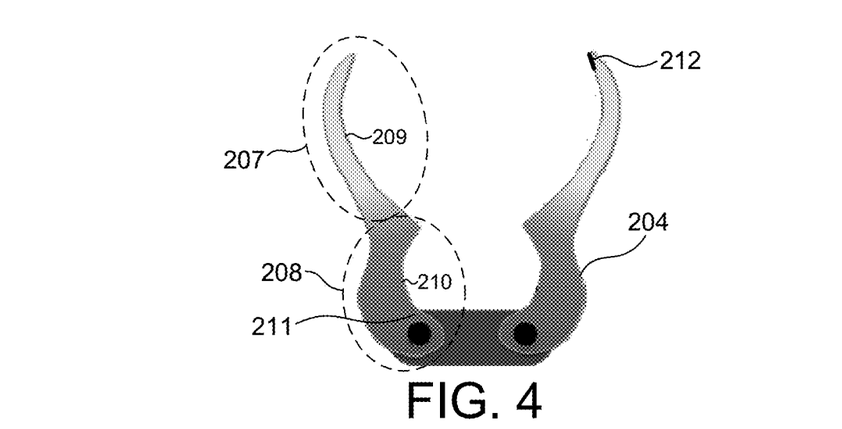
FIGS. 4-6 depict gripper actuator 204 in different operational scenarios.
Figure 5:
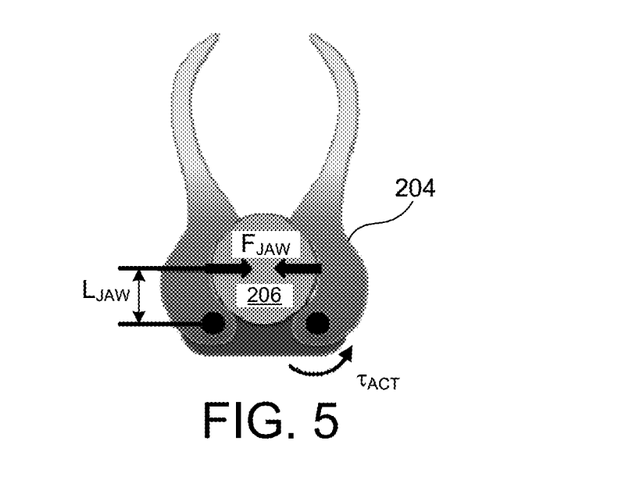
Figure 6:
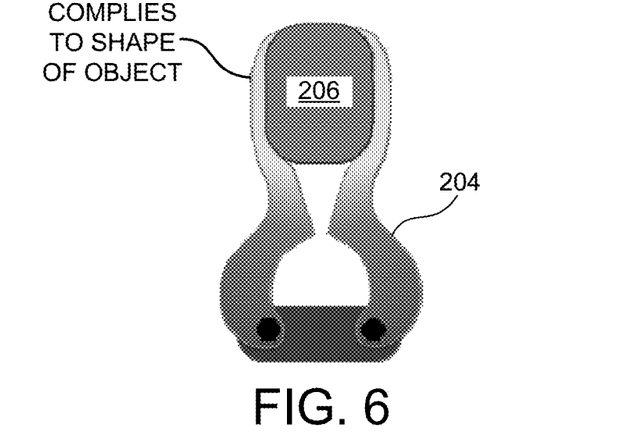

Wearable gripper device 200 is designed to bear a large load to support a person using a walker or a cane, and hold various objects having diverse shapes and physical properties. In some embodiments, a gripper actuator includes two or more fingers, each having a location dependent shape profile and compliance to accommodate different manipulation tasks. FIGS. 4-6 depict gripper actuator 204 in different operational scenarios. As depicted in FIG. 4, gripper actuator 204 includes two fingers. The pair of fingers is opened and closed for grasping and releasing an object. Each finger includes a portion 208 constructed from strong, stiff material having a shape profile 210 that complements the round profiles of the handle of a walker or a cane. Portion 208 of each finger is located closest to the rotary joint 211 associated with the finger such that the maximum amount of gripping force is generated for a given amount of actuator torque. As depicted in FIG. 5, portions 208 of both fingers are used for grasping a round object 206 such as a walker. $L_{jaw}$, is the distance from the center of rotation 211 of the finger to the middle of the radius of shape profile 210. $\tau_{jaw}$ is the torque applied at the center of rotation by an actuator rotating the fingers. Since $L_{jaw}$ is relatively small, the grasp force, $F_{jaw}$, in the middle of portion 208 of the finger is relatively large (i.e., $F_{jaw}=\tau_{jaw}/L_{jaw}$). As depicted in FIG. 4, each finger includes a portion 207 constructed from compliant material having a shape profile 209 that complements a variety of differently shaped objects. Portion 207 of each finger is located furthest from the rotary joint 211 associated with the finger such that a reduced amount of gripping force is generated for a given amount of actuator torque, compared to portion 208. The compliance and shape profile 209 of portion 207 allow the fingers to adapt to fit the shape of various objects. For example, FIG. 6 depicts the fingers of gripper actuator 204 wrapping around an object 206. Portion 207 is long enough to wrap around objects and effectively increase the area of contact between the gripper actuator 204 the object under grasp.

Figure 7:
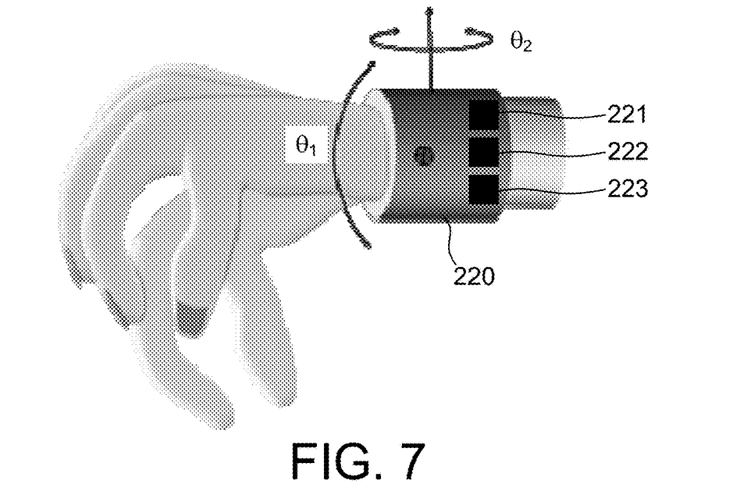
FIGS. 7-9 depict an instrumented wristband device 220 in at least one novel aspect.
Figure 8:
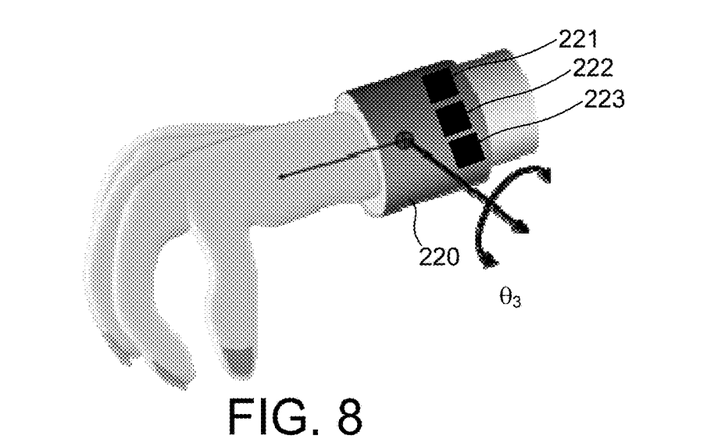
Figure 9:
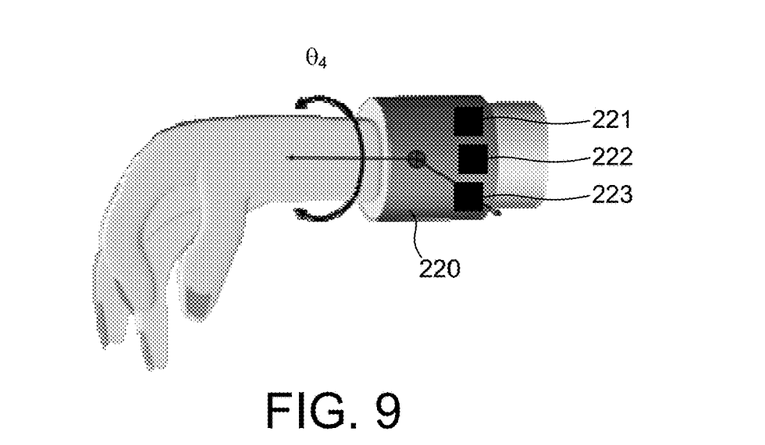

FIGS. 7-9 depict an instrumented wristband device 220 in at least one novel aspect. In some embodiments, instrumented wristband 220 includes haptic feedback device 221 and gesture sensors, such as an inertial measurement unit (IMU) 222, and a wrist goniometer 223. The instrumented wristband device 220 does not cover the fingertips, nor does it interfere with movements of the fingers and palm. The instrumented wristband device 220 is configured to detect movements of a user. The signals generated by the instrumented wristband device 220 are received by a WGCPMM, such as WGCPMM 101, and used as the basis for controlling a wearable gripper device, such as wearable gripper device 200 depicted in FIG. 2. In some embodiments, instrumented wristband device 220 includes a WGCPMM, such as WGCPMM 101, to process measurement signals and supply power to elements such as haptic feedback device 221, inertial measurement unit (IMU) 222, and wrist goniometer 223.

As depicted in FIG. 7, an instrumented wristband device 220 is wrapped around the wrist of a user. Haptic feedback device 221 is integrated with the instrumented wristband 220 such that a vibration, or other physical signal generated by the haptic feedback device, is physically communicated to the user. In one example, the amplitude of the vibration generated by haptic feedback device 221 is indicative of the grip force generated at the fingers of a wearable gripper device, such as wearable gripper device 200. In another example, the frequency of the vibration generated by haptic feedback device 221 is indicative of the grip force generated at the fingers of a wearable gripper device, such as wearable gripper device 200. In this example, torque signals generated by the actuators of gripper actuator 204, or direct force measurements performed by force sensors (e.g., force sensors 121 depicted in FIG. 1) embedded in the gripper are communicated to WGCPMM 101. In response, WGCPMM 101 generates control commands communicated to haptic feedback device 221 that cause the device to vibrate with amplitude proportional to the estimated grip force.

Instrumented wristband 220 is configured to detect hand flexion, $\theta_1$, radial/ulnar deviation, $\theta_2$, forearm tilt, $\theta_3$, and pronation/supination, $\theta_4$, based on signals provided by IMU 222 and wrist goniometer 223 as depicted in FIGS. 7-9.

Figure 10:
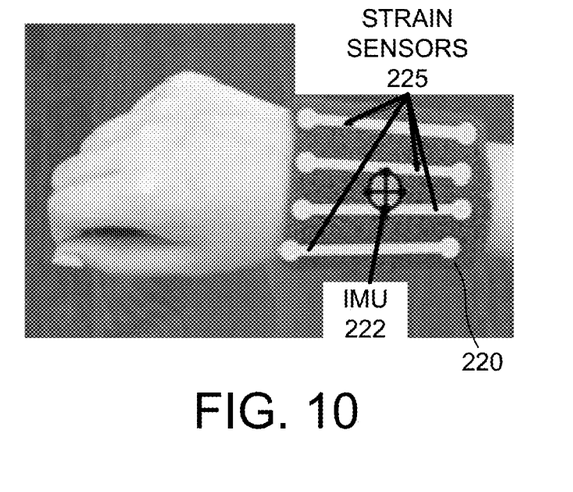
FIG. 10-13 depict an embodiment of an instrumented wristband device including a two-axis wrist goniometer based on a number of strain sensors and an inertial measurement unit.
Figure 11:
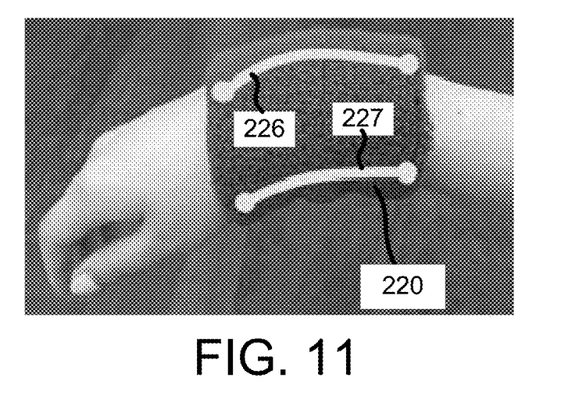
Figure 12:
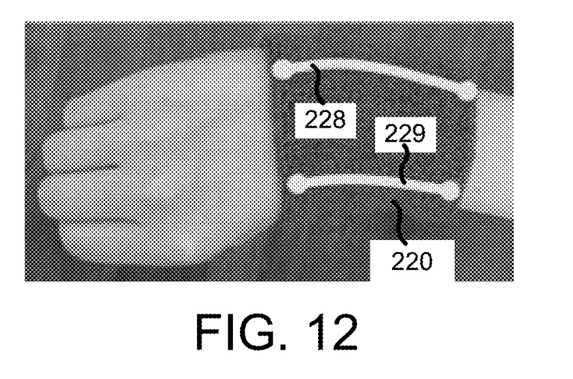
Figure 13:
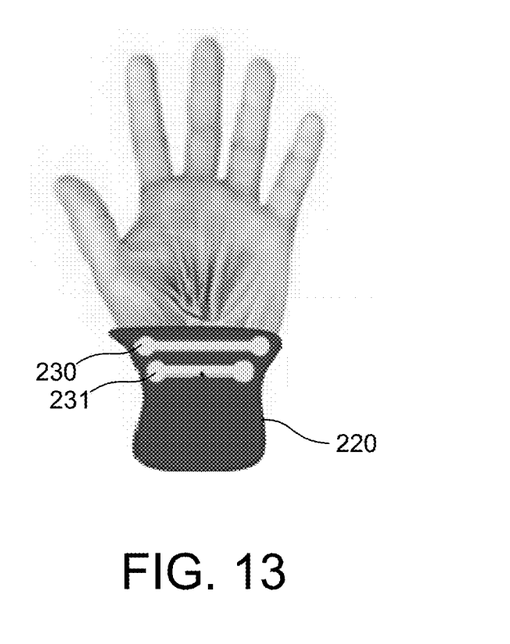

FIG. 10 depicts one embodiment of instrumented wristband device 220 including a two-axis wrist goniometer based on a number of strain sensors 225 and IMU 222. The goniometer measures the wrist flexion/extension angle, $\theta_1$, for example as a function of differential strain detected by strain sensors 226 and 227, as depicted in FIG. 11. In addition, the goniometer measures the radial/ulnar deviation angle, $\theta_2$, for example, as a function of differential strain detected by strain sensors 228 and 229, as depicted in FIG. 12. The pronation/supination angle, $\theta_4$, is measured with a three-axis micro-electromechanical system (MEMS) accelerometer built into the IMU 222. These three angles are the basic measures of hand posture used for controlling the gripper. However, the measurement of additional angles may improve control of the gripper. In one example, the forearm tilt angle, $\theta_3$, is measured by IMU 222. In other examples, gestures and signaling movements, such as swinging of the hand and tapping of an object with the hand are measured by processing the six channels of available IMU signals. In another example, a set of strain sensors 230 and 231 are distributed over the wrist area to measure thumb abduction/adduction as depicted in FIG. 13.

Although FIGS. 10-13 depict particular arrangements of strain sensors for illustrative purposes, in general, any suitable number and arrangement of strain sensors employed to perform wrist joint measurements may be contemplated within this patent document. The human wrist is anatomically complex. An optimal location and distribution of sensor strips may be determined by building a data-driven model to predict wrist joint displacements for a given set of sensor strip locations. Sensitivity, orthogonality, collinearity, and prediction error covariance are evaluated to find an optimal arrangement of multiple sensor strips. Redundant sensor strips may be employed to improve measurement robustness.

In the embodiment depicted in FIGS. 10-13, the wrist goniometer includes several strain sensors. The strain sensors may be constructed from materials that exhibit changes in electric resistance or capacitance as a function of strain. The wristband itself is flexible so that it does not impede the wrist bending motion. The portion of the surface of the wristband that contacts the skin is treated with a material, e.g., sticky rubber material, which prevents the wristband from slipping on the skin as the wrist bends. In some embodiments, the strain sensors are woven into, or otherwise integrated with, the wristband.

In another further aspect, a number of conductive, stretchable string sensors wrapped around the hand or fingers of a user are employed to estimate wrist and hand motion. FIGS. 14A-B, 15, and 16 depict various embodiments of an instrumented wristband device 240 employing conductive, stretchable string sensors. In some embodiments, instrumented wristband device 240 includes a WGCPMM, such as WGCPMM 101, to process measurement signals and supply power to conductive, stretchable string sensors.

Figure 14A:
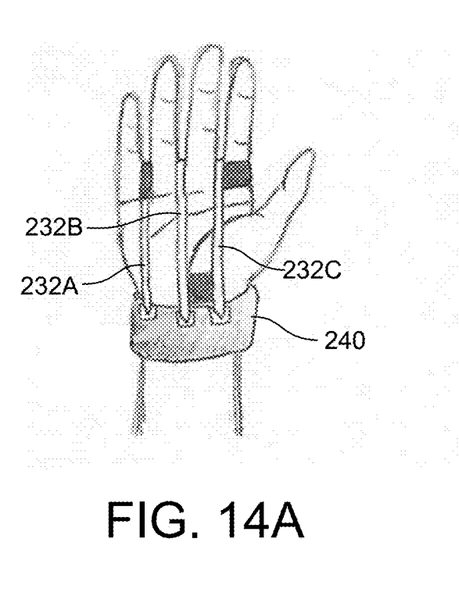
FIG. 14A depicts an instrumented wrist device from a viewpoint that includes the front side of the hand.
Figure 14B:
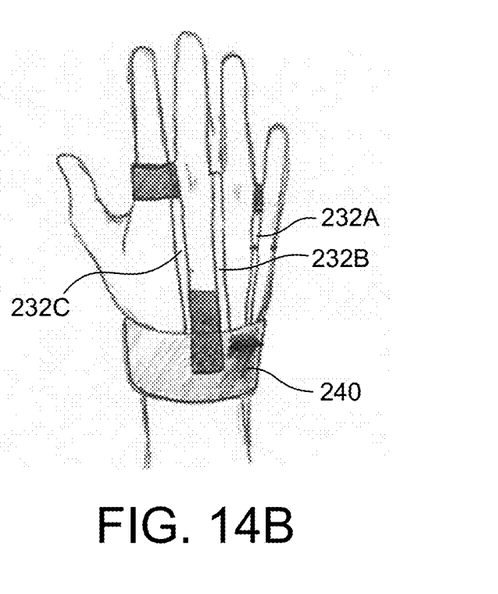
FIG. 14B depicts the instrumented wristband device depicted in FIG. 14A from a viewpoint that includes the back side of the hand.

FIG. 14A depicts an instrumented wristband device 240 from a viewpoint that includes the front side of the hand. As depicted in FIG. 14A, instrumented wristband device 240 includes conductive, stretchable string sensors 232A-C that wrap over the hand between the fingers. FIG. 14B depicts the instrumented wristband device 240 from a viewpoint that includes the back side of the hand to further illustrate the wrapping of the stretchable string sensors 232A-C over the hand between the fingers. The conductive, stretchable string sensors 232A-C strings cause minimal disruption to hand operation, allowing the wearer to perform many hand tasks in a normal fashion. The string sensors are coated with a dielectric material so that the user can come into contact with water, e.g., handwashing, etc., without having to remove the string sensors.

Figure 15:
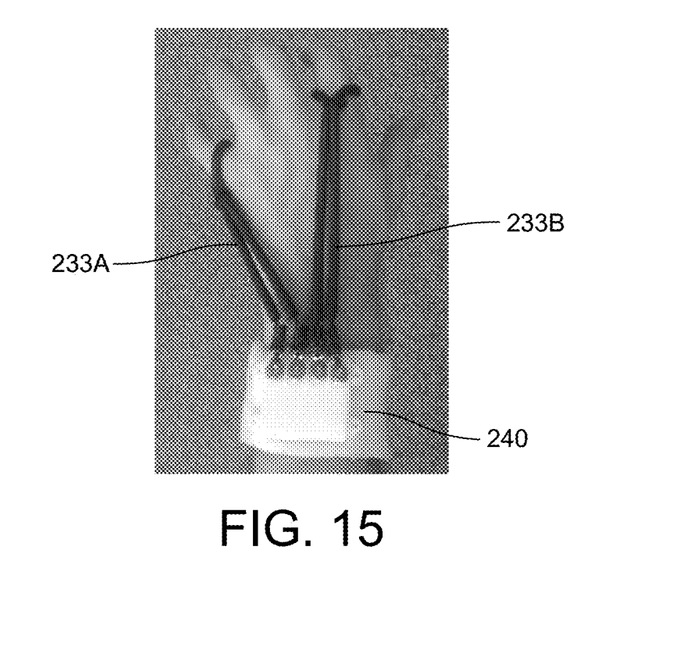
FIG. 15 depicts an instrumented wristband device 250 employing conductive, stretchable string sensors in another embodiment.

FIG. 15 depicts an instrumented wristband device 250 employing conductive, stretchable string sensors in another embodiment. As illustrated in FIG. 15, conductive, stretchable string sensors 233A and 233B are located on the hand around the fingers. In this manner, the conductive, stretchable string sensors 233A and 233B are easily removable, even by users having impaired hand dexterity. As each finger flexes the conductive stretchable string sensors 233A-B extend and retract, changing their electrical resistance. Each conductive, stretchable string sensor is encapsulated with a watertight tube that allows the user to come into contact with water without removing the sensor.

Figure 16:
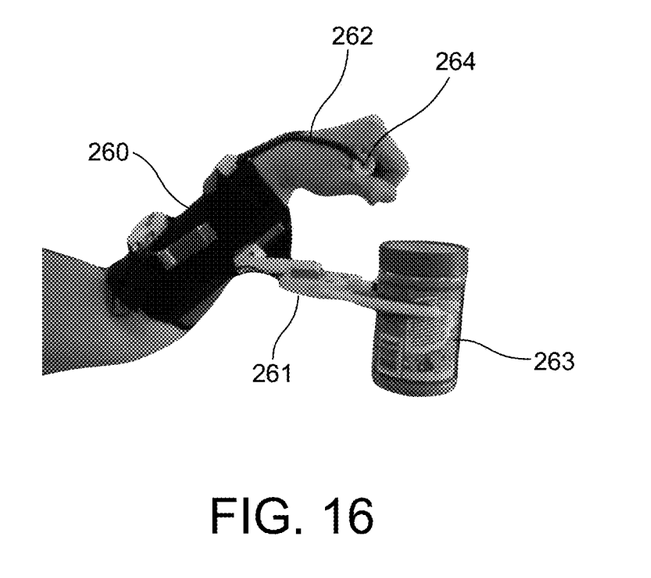
FIG. 16 depicts a wearable gripper system 260 in another embodiment.

FIG. 16 depicts a wearable gripper system 260 in another embodiment. Wearable gripper system 260 includes a wearable gripper 261 grasping an object 263. Conductive, stretchable string sensors 262 are employed to measure hand motion. In one aspect, one or more of the conductive, stretchable string sensors 262 are passed through a tube structure 264 that is held across the palm of the hand of the user. In this manner, the conductive, stretchable string sensors 262 are sensitive to changes in hand motion when a user squeezes the tube structure 264. In some embodiments, the displacement of the hand caused by the squeezing motion of the user is measured by conductive, stretchable string sensors 262. A WGCPMM, such as WGCPMM 101 determines a desired gripping force based on the measured displacement, and communicates control signals to wearable gripper 261 that cause the wearable gripper 261 to exert the desired gripping force.

In the embodiments, depicted in FIGS. 14-16, the electrical resistance of the conductive strings varies as they are stretched due to changes in hand configuration. The conductive strings are attached to an instrumented wristband including integrated electronics that measure the resistance values of the conductive strings. Control commands are determined based on the measured values.

In some embodiments, an adaptive algorithm is implemented by a WGCPMM, such as WGCPMM 101, that can effectively interpret hand gesture based on string resistance values. The adaptive algorithm includes a learning process to correctly identify hand gestures based on resistance training data collected from during the learning process.

In some embodiments, a radio frequency transmitter embedded in the wristband transmits hand gesture signals to an external computing device (e.g., a computer, a mobile phone, a robot or any other electronic device in the vicinity).

In a further aspect, a wearable gripper is controlled based on measurement signals generated by an instrumented wristband device. Control algorithms translate wristband sensor signals to gripper motion commands such that the correlation between gesture and gripper motion is intuitive. In this manner, the interface between a user and a wearable gripper system is natural and easy to use. In a further aspect, the control algorithms which translate wristband sensor signals to gripper motion commands are different depending on the disability level of each user.

In some operational scenarios, a hemiplegic and hemiparetic patient is unable to control the motion of the fingers of an affected hand, but is able to move both the arm and wrist. In this scenario, the wearable gripper is attached to the forearm of the affected side, and the instrumented wristband sensor is attached to the wrist of the affected arm.

In one embodiment, the kinematic structure of the wearable gripper described with reference to FIG. 2 and the anatomic structure of the human wrist and forearm are related as follows: The second joint of the wearable gripper, $J_2$, is controlled based on the wrist flexion/extension angle, $\theta_1$, as described with reference to FIGS. 7-9. The third joint of the wearable gripper, $J_3$, is controlled based on the wrist pronation/supination angle, $\theta_4$, as described with reference to FIG. 9. In this manner, wearable gripper and the wrist rotate in the same directions, so it is intuitive and easy to operate. Similarly, there is a direct relationship between a particular wrist angle measured by the instrumented wristband device and a control command communicated to a particular actuator of the wearable gripper device.

The fingers of the affected hand cannot be used to generate a command to open and close the gripper actuator because the user lacks control over the fingers in this scenario. However, in some embodiments, the opening and closing of the gripper actuator (i.e., joint, $J_4$) is controlled based on the radial/ulnar deviation angle, $\theta_2$. In some other embodiments, the opening and closing of the gripper actuator is controlled based on the forearm orientation angle, $\theta_3$. The prismatic joint of the wearable gripper, $J_1$, depicted in FIG. 2, is controlled based on the remaining measured angle. Thus, in some embodiments, the prismatic joint of the wearable gripper, $J_1$, is controlled based on the radial/ulnar deviation, $\theta_2$. In some other embodiments, the prismatic joint of the wearable gripper, $J_1$, is controlled based on the forearm orientation angle, $\theta_3$.

As described hereinbefore, the opening and closing of the gripper actuator (i.e., joint, $J_4$) is controlled based on either the radial/ulnar deviation angle, $\theta_2$, or the forearm orientation angle, $\theta_3$, before contact is made with an object. However, after contact is made with an object it becomes important to control the grasp force. For example, when holding a walker rail or a cane handle, a user must be able to determine whether sufficient grasp force is generated by the wearable gripper. In some embodiments, a motor current measurement technique is employed, for example, by WGCPMM 101, to estimate the grasp force at joint, $J_4$. WGCPMM 101 communicates an indication of the estimated grasp force to the user by a haptic rendering technique. In some embodiments, a small vibrator is employed as a haptic feedback device as depicted in FIGS. 7-9. The vibration amplitude or frequency is employed as an indicator of the grasp force. In one example, the user is notified whether the walker rail has been grasped with sufficient force based on the vibratory feedback.

Similarly, the haptic feedback technique described herein may be employed as an indicator of grasp force generated by the gripper actuator when manipulating objects with the compliant portion of the gripper fingers (e.g., portions 207 of the gripper fingers depicted in FIG. 4).

In a further aspect, a force sensor is located on the gripper to measure the amount of force applied by the gripper onto the object. In some embodiments, the measured force is read from the force sensor, for example, by WGCPMM 101, and a visual indication of the measured force is rendered on a display device (e.g., LCD display) that is part of the wearable gripper system as depicted in FIG. 1. This visual indication allows the user to monitor the amount of force being applied to an object and prevent the exertion of excessive force. In some other embodiments, the measured force is read from the force sensor and a haptic rendering is employed to communicate an indication of the measured force to the user.

In some other operational scenarios, a hemiplegic and hemiparetic patient is unable to control the motion of the fingers and wrist of an affected hand, but is able to move the arm. In this scenario, the wearable gripper is attached to the forearm of the affected side, but the instrumented wristband sensor is attached to the wrist of the unaffected arm.

A hemiplegic and hemiparetic patient is able to control the motion of the fingers, wrist, and arm of the unaffected hand. In these operational scenarios it is desirable to measure a limited set of finger movements and use these finger movements to control the motion of joint $J_4$ of the wearable gripper located on the affected hand. In some embodiments, thumb abduction/adduction is measured by strain sensors located transversely along the transverse carpal ligament, as depicted in FIG. 13. The thumb metacarpal bone rotates about a carpometacarpal joint at the wrist. The instrumented wristband extends towards the thumb so that motion at the root of the thumb near the wrist is measureable. In some embodiments, relative motion between the thumb and little finger is measured and these measurements are used to control the motion of joint $J_4$ of the wearable gripper.

In scenarios where the wearable gripper is attached to the forearm of the affected side, but the instrumented wristband sensor is attached to the wrist of the unaffected arm, the unaffected hand may perform a task, while the wearable gripper holds an object. In this scenario, the unaffected hand plays two different roles. The unaffected hand is employed to control the motion of the gripper and to execute a manipulative task. To avoid confusion, the two roles are executed in series. A user interacts with a mode control device (e.g., voice activated switch, a mechanical switch or button, a simple gesture, etc.) located on the wearable gripper system to select one of two operational modes. In one mode, wearable gripper is under control based on hand motions sensed by the instrumented wristband device as described hereinbefore. In a second mode, the wearable gripper is released from control based on signals detected by the instrumented wristband. In this mode, a user is free to manipulate the unaffected hand without triggering any control action on the part of the wearable gripper. In one example, a user selects a mode that engages the instrumented wristband sensor in the control of the wearable gripper. The user directs the gripper to grasp a can. Next, the user selects a mode that disengages the instrumented wristband sensor from control of the wearable gripper. During this mode, the wearable gripper maintains its grasp of the can while the user removes a lid from the can using the unaffected hand. Next, the user selects a mode that engages the instrumented wristband sensor in the control of the wearable gripper and releases grasp of the can by the gripper.

In another further aspect, the wearable gripper device includes one or more temperature sensors to detect the temperature of objects in contact with the wearable gripper. In one example, one or more temperature sensors 212 are embedded in the tip of one or more of the gripper fingers as depicted in FIG. 4. A user directs the gripper finger to make contact with an object having an unknown temperature. The temperature measured by the temperature sensor 212 is received by a WGCPMM, such as WGCPMM 101. The WGCPMM communicates signals to a display device (e.g., display device 161 depicted in FIG. 1) that cause the display device to render a visual indication of the measured temperature. This visual indication allows the user to monitor the temperature of objects in the environment and makes the user aware of objects having excessively high temperatures in the surrounding environment. In some other embodiments, the measured temperature is read from the temperature sensor and a haptic rendering is employed to communicate an indication of the measured temperature to the user. In some embodiments a warning indicator (e.g., flashing light, audible tone, etc.) is triggered when a measured temperature exceeds a predetermined threshold value.

In another further aspect, an image capture device 123 is located on the gripper. In one example, the image capture device 123 collects images of medicine labels and transmits the images electronically to health care providers for verification or refill. In another example, the image capture device 123 collects images and the images are rendered on a large format, external display device (not shown). In this manner, users with impaired vision are able to view large format images of their surroundings.

Figure 17:
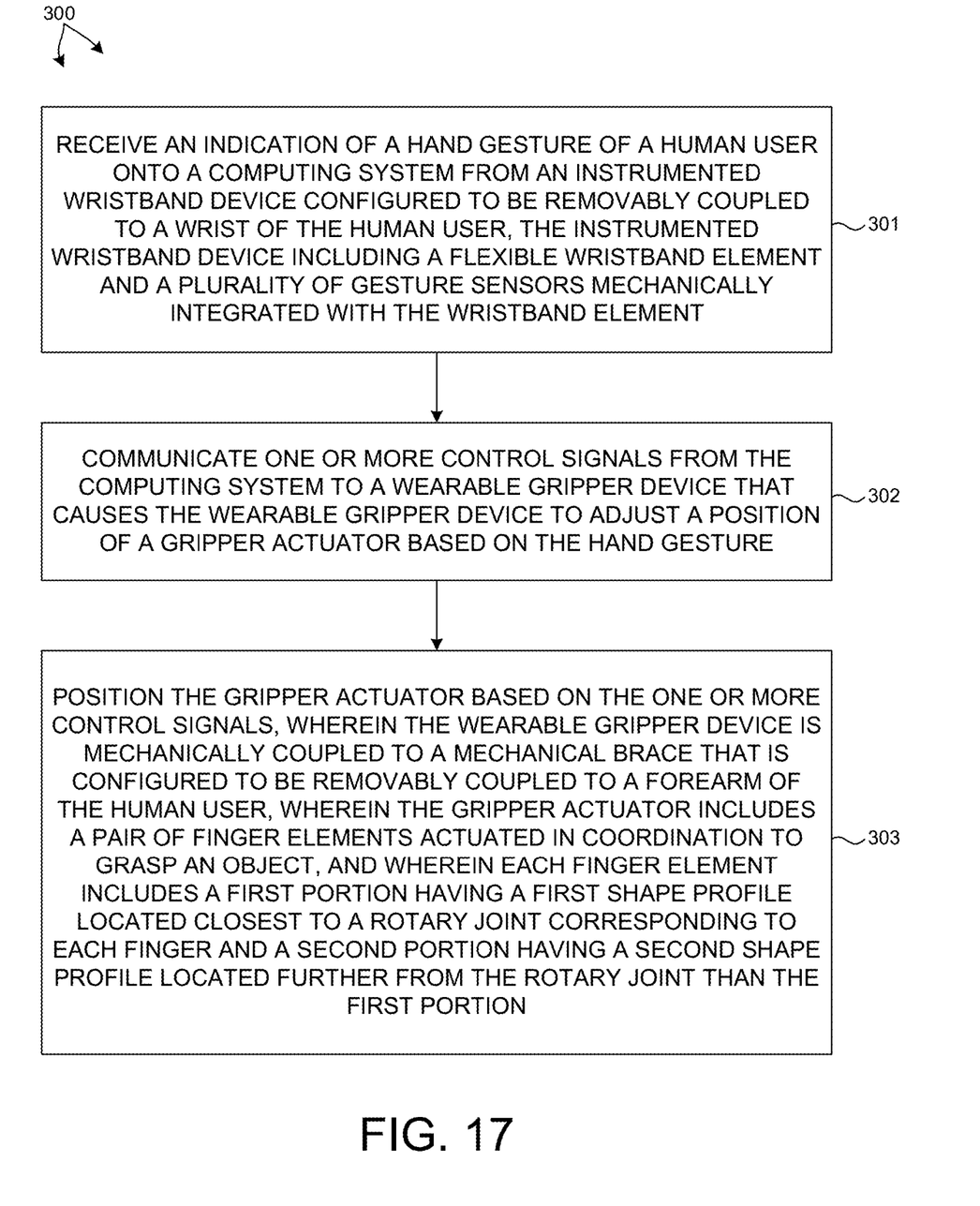
FIG. 17 illustrates a flowchart of a method 300 implementing wearable gripper control and power management functionality as described herein.

FIG. 17 illustrates a flowchart of a method 300 implementing wearable gripper control and power management functionality as described herein. In some embodiments, WGCPMM 101 is operable in accordance with method 300 illustrated in FIG. 17. However, in general, the execution of method 300 is not limited to the embodiments of WGCPMM 101 described with reference to FIG. 1. This illustration and corresponding explanation are provided by way of example as many other embodiments and operational examples may be contemplated.

In block 301, an indication of a hand gesture of a human user is received onto a computing system from an instrumented wristband device. The instrumented wristband device is configured to be removably coupled to a wrist of the human user. The instrumented wristband device includes a flexible wristband element and a plurality of gesture sensors mechanically integrated with the wristband element.

In block 302 one or more control signals are communicated from the computing system to a wearable gripper device. The control signals cause the wearable gripper device to adjust a position of a gripper actuator based on the hand gesture.

In block 303, the gripper actuator is positioned based on the one or more control signals. The wearable gripper device is mechanically coupled to a mechanical brace that is configured to be removably coupled to a forearm of the human user. The gripper actuator includes a pair of finger elements actuated in coordination to grasp an object. Each finger element includes a first portion having a first shape profile located closest to a rotary joint corresponding to each finger and a second portion having a second shape profile located further from the rotary joint than the first portion.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A wearable gripper system, comprising:
   a mechanical brace configured to be removably coupled to a forearm of an affected arm of a human user;
   a wearable gripper device mechanically coupled to the brace, the wearable gripper device including a gripper actuator having two or more finger elements actuated in coordination to grasp an object;
   an instrumented wristband device configured to be removably coupled to a wrist of the affected arm of the human user, the instrumented wristband device including a flexible wristband element and one or more gesture sensors including an inertial measurement unit integrated with the wristband element, the instrumented wristband configured to measure a wrist angle of the human user and transmit an indication of the wrist angle of the human user; and a computing system communicatively coupled to the wearable gripper device and the instrumented wristband device, wherein the computing system is configured to:

receive the indication of the wrist angle of the human user from the instrumented wristband device, and communicate one or more control signals to the wearable gripper device that causes the wearable gripper device to adjust a position of a gripper actuator.

2. The wearable gripper system of claim 1, wherein the one or more gesture sensors also include a plurality of strain sensors.

3. The wearable gripper system of claim 2, further comprising:

a haptic feedback device coupled to the instrumented wristband device, wherein the computing system is communicatively coupled to the haptic feedback device, and wherein the computing system is further configured to:

receive an indication of any of a grip force exerted by the gripper actuator measured by a grip sensor and a temperature of an object measured by a temperature sensor, and communicate one or more signals to the haptic feedback device that causes the haptic feedback device to change an amplitude or frequency of a vibration generated by the haptic feedback device in response to the received indication of any of the grip force exerted by the gripper actuator and the temperature of an object measured by the temperature sensor.

4. The wearable gripper system of claim 1, wherein each finger element includes a first portion having a first shape profile located closest to a rotary joint corresponding to each finger and a second portion having a second shape profile located further from the rotary joint than the first portion, and wherein the second portion of each finger element having the second shape profile has greater mechanical compliance than the first portion of each finger element having the first shape profile.

5. The wearable gripper system of claim 1, wherein the computing system is further configured to:

communicate one or more control signals to the wearable gripper device that cause the wearable gripper device to grip an object with a grip force within a desired force range.

6. The wearable gripper system of claim 1, wherein there is a direct relationship between the wrist angle measured by the instrumented wristband device and a control command communicated to the wearable gripper device that causes the wearable gripper device to adjust a position of the gripper actuator.

7. The wearable gripper system of claim 1, further comprising:

a display device communicatively coupled to the computing system, and wherein the computing system is further configured to:

receive an indication of any of a grip force exerted by the gripper actuator measured by a grip sensor and a temperature of an object measured by a temperature sensor, and communicate one or more signals to the display device that causes the display device to render an image indicative of any of the grip force exerted by the gripper actuator and the temperature of an object measured by the temperature sensor.

* * * * *